United States Patent [19]

Kelly, Jr. et al.

[11] Patent Number: 4,757,258
[45] Date of Patent: Jul. 12, 1988

[54] PROBE CARRIER SYSTEM FOR INSPECTING BOILER TUBES

[75] Inventors: Raymond G. Kelly, Jr., Pittsburgh; Phillip J. Hawkins, Penn Hills Township, Allegheny County; Bruce W. Bevilacqua, Penn Township, Westmoreland County, all of Pa.

[73] Assignee: Westinghouse Electric Corp., Pittsburgh, Pa.

[21] Appl. No.: 802,556

[22] Filed: Nov. 27, 1985

[51] Int. Cl.$^4$ .................. G01N 27/90; B65H 59/00; H02G 1/08; B25J 11/00
[52] U.S. Cl. .................. 324/220; 165/11.2; 254/134.3 FT; 254/134.5; 414/749; 901/44
[58] Field of Search ............... 324/219–221; 73/622, 623; 165/11.2; 414/749; 376/245, 249, 254; 254/134.3 CL, 134.3 FT, 134.5; 901/44, 46

[56] References Cited

U.S. PATENT DOCUMENTS

| | | | |
|---|---|---|---|
| 2,148,982 | 2/1939 | Erikson | 254/134.5 |
| 4,050,384 | 9/1977 | Chapman | 254/134.5 X |
| 4,087,748 | 5/1978 | Pigeon et al. | 324/220 |
| 4,131,018 | 12/1978 | Muller et al. | 324/220 X |
| 4,178,875 | 12/1979 | Moschetti | 324/220 X |
| 4,389,611 | 6/1983 | Pigeon et al. | 324/220 |
| 4,438,805 | 3/1984 | Gugel | 165/11.2 X |
| 4,494,907 | 1/1985 | Coussau et al. | 324/220 X |
| 4,505,323 | 3/1985 | de la Pintiere et al. | 165/11.2 |
| 4,560,931 | 12/1985 | Murakami et al. | 324/220 |
| 4,569,230 | 2/1986 | Asty et al. | 73/623 |
| 4,633,177 | 12/1986 | David et al. | 324/220 |

FOREIGN PATENT DOCUMENTS

| | | | |
|---|---|---|---|
| 0033785 | 3/1977 | Japan | 324/219 |
| 0026256 | 2/1983 | Japan | 324/220 |
| 313679 | 8/1969 | Sweden | 324/220 |
| 0844451 | 7/1981 | U.S.S.R. | 324/220 |

Primary Examiner—Gerard R. Strecker

[57] ABSTRACT

An inspection system and process for inspecting a plurality of conduits mounted in a manifold is disclosed herein. The system generally comprises a probe carrier for driving an eddy current or ultrasonic probe throughout the conduits to be inspected, and a delivery assembly detachably mountable within the manifold for remotely delivering and inserting the probe carrier into the open ends of the conduits. The delivery system includes an insertion and pusher mechanism for selectively inserting and pushing the probe carrier through the open ends of the tubes, a rail assembly which is removably mountable within the manifold, and a carriage slidably mounted on the rail assembly for supporting and axially positioning the insertion and pusher mechanism. Angular and axial electric drive motors are also provided for rotating and moving the insertion and pusher to a selected angle around and point along the longitudinal axis of the manifold. Finally, the system includes a control system having a television camera for allowing the insertion and pusher mechanism to be positioned by remote control, as well as a computer and first and second encoders operatively connected to the angular and axial drive motors for mapping the locations of the open ends of the tubes prior to the inspection operation. The invention is particularly useful in inspecting the boiler tubes mounted in a mud drum in a fossil fuel electrical power plant.

32 Claims, 8 Drawing Sheets

PROBE CARRIER SYSTEM FOR INSPECTING BOILER TUBES

BACKGROUND OF THE INVENTION

1. Field of the Invention

This invention is both a system and a process for inspecting a plurality of conduits, each of which includes an open end mounted in a manifold. It is particularly useful in inspecting the boiler tubes of a fossil fuel electrical power plant, where each of the tubes has an open end mounted in a cylindrical mud drum.

2. Description of the Prior Art

Systems and processes for inspecting the boiler tubes in fossil fuel steam generators are known in the prior art. Such systems and processes generally involve the shutdown of the boiler, and the construction of an array of scaffolds around the tubes to be inspected. After the scaffolding has been completed, the outside surfaces of the tubes are ultrasonically and visually inspected, and the locations of damaged or corroded sections of these tubes are recorded. The damaged or corroded tube sections are then repaired, the scaffolding disassembled, and the boiler re-fired.

Unfortunately, such prior art systems have a number of shortcomings which have yet to be solved in the prior art. For example, it usually takes about three weeks to build the scaffolding and to complete an inspection of a typical fossil fuel steam boiler when such prior art systems are used. This necessitates three weeks of down time for the electrical generators which are driven by the steam boiler under inspection, which in turn results in a substantial loss of revenues. Additionally, the resulting inspection often fails to locate the sections of some of the tubes which are in need of repair due to the fact that many of the tubes are closely packed together, and take more than one 160° turn throughout their lengths. Hence, some portions of the tubes are simply not visible or accessible to an inspector, regardless of how well positioned the scaffolds are. Also, since only the outside surfaces of these tubes may be inspected with such prior art methods, extensive cracking or corrosion which occurs on the inside of the tubes will not be detected by the inspectors unless it has worked its way completely through the tubes.

While robotically-movable eddy current probes for inspecting the inside walls of heat exchange tubes of nuclear steam generators are also known in the prior art, the systems which employ such probes would not be functional in a fossil fuel boiler for a number of reasons. First, the heat exchange tubes in nuclear steam generators each have an open end which is mounted in a flat tubesheet which may be accessed through a manway in the primary side of the generator. While the boiler tubes in fossil fuel generators likewise have an open end which is accessible through a manway, the open ends of such tubes are mounted around the axis of a cylindrical mud drum in a spoke-like pattern which is frequently irregular. Moreover, the inner dimensions of such mud drums (i.e., 40 feet long and only 14 inches in diameter throughout much of its length) would not give a probe operator or any known robotic system a sufficient amount of room to crawl through the drum and to sequentially insert an eddy current probe throughout each of the open ends of the tubes. And even if the mud drum had a larger diameter throughout its entire 40 foot length, the time it would take to snake such a probe either manually or robotically up through each of the 220-foot-long, zig-zagging tubes would be prohibitive, if it could be accomplished in this manner at all.

Accordingly, there is clearly a need for some sort of inspection system and process which is capable of inspecting the boiler tubes in a fossil fuel power plant with a minimum amount of time and effort, and a maximum amount of reliability and accuracy. Such a system should be capable of inspecting each of the tubes from its inside wall, so that damage caused by internal corrosion, pitting, or cracking could be repaired before it had an opportunity to completely penetrate the tube walls. Ideally, such a system should be capable to inspecting each boiler tube throughout its entire length, regardless of its position with respect to adjacent boiler tubes, and regardless of how many bends it may have along its length.

SUMMARY OF THE INVENTION

In its broadest sense, the invention is both a system and process for inspecting a plurality of conduits wherein each conduit has an open end mounted in a manifold. The system generally comprises a probe carrier which is insertable within the open ends of each of these conduits, and a delivery assembly mountable within the manifold for remotely delivering the probe carrier into the open end of a selected one of the conduits. The invention finds particular utility in inspecting the boiler tubes in a fossil fuel power plant, where each of the tubes has an open end mounted in an elongated, cylindrical mud drum.

The delivery assembly may include a probe insertion and pusher means coupled to an angular and axial drive means for aligning the probe carrier with the open end of a selected tube, and inserting the probe carrier into the tube. The angular drive means may include a stepping motor and pinion gear arrangement for rotating the probe insertion and pusher means to a selected angle around the longitudinal axis of the manifold. The axial drive means may include a rail assembly which is removably mountable along the longitudinal axis of the manifold, and a carriage slidably mounted on the rail assembly for supporting the insertion and pusher means. The rail assembly is preferably formed from a plurality of elongated rail members, each of which includes a pair of legs of adjustable length which terminate in electromagnets so that the rail member may be detachably mounted in tandem in the manifold along its longitudinal axis. A separate stepping motor and rack-and-pinion arrangement may be included to control the movement of the carriage along the rail members forming the rail assembly.

The inspection system may further have a control system for remotely controlling the carrier delivery assembly. This control system may include a television camera so that an operator may remotely position the probe insertion and pusher means by selectively actuating the stepping motors of the angular and axial drive means. The control system may further include a mapping means for mapping and storing the cylindrical coordinates of each of the open ends of the conduits to be inspected prior to the inspection operation. In the preferred embodiment, the mapping means includes first and second encoders mechanically linked to the stepping motors of the angular and axial drive means, respectively, as well as a computer circuit whose input is electrically connected to the output of the encoders.

The probe carrier of the inspection system may include an eddy current probe or ultrasonic probe, a drive means including at least one drive wheel for moving the carrier along the longitudinal axis of the conduit, as well as a housing for containing both the probe and the drive means. The probe carrier may further be connected to flexible member such as a cable which is simultaneously pushed by the probe insertion and pusher means while the drive wheel is in operation in order to assist the drive means of the probe carrier in moving the carrier along the longitudinal axis of the conduit. The drive wheel may be powered by a pneumatic motor, and the cable which is connected to the probe carrier functions as an air line to this motor. The probe carrier may further include a load wheel assembly which includes at least one radially extensible load wheel rotatably mounted on the opposite side of the drive wheel for selectively biasing the drive wheel against the inner surface of the conduit. In the preferred embodiment, the load wheel assembly includes a hydraulic piston both for radially extending the load wheel, and for resiliently biasing it against the inner wall of the conduit.

In the process of the invention, the rail members of the carrier delivery system are detachably mounted in tandem along the longitudinal axis of the manifold. Next, the location of each of the open ends of the conduits is mapped by locating each of the conduit ends with the television camera of the control circuit, sequentially aligning the probe insertion and pusher means with each of these open ends by remotely controlling the angular and axial drive means, and recording the cylindrical coordinates of each of these open ends into the memory of the computer circuit. After this mapping step has been completed, the computer positions the insertion and pusher means so that it automatically inserts the probe carrier into one of the open ends of the conduits. The probe carrier is driven substantially through the entire length of the conduit by simultaneously actuating the drive means of the carrier and pushing the pneumatic power cable attached to the probe carrier by the insertion and pusher means. After the probe carrier has been inserted substantially through the conduit to be inspected, the drive means of the probe carrier is deactuated, and the probe carrier is pulled back to the insertion means by reeling back the pneumatic cable. While the probe carrier is being withdrawn in this manner, the eddy current probe contained within the probe carrier is actuated so that imperfections in the metallic walls of the conduits may be detected. The process is repeated for each of the conduits mounted in the manifold.

BRIEF DESCRIPTION OF THE SEVERAL FIGURES

FIG. I is a schematic side view of a typical fossil fuel steam boiler having a boiler water wall formed from an array of zig-zagging boiler tubes.

DETAILED DESCRIPTION OF THE PREFERRED EMBODIMENT

General Overview of the Purpose, Structure and Function of the Invention

Figure 1:
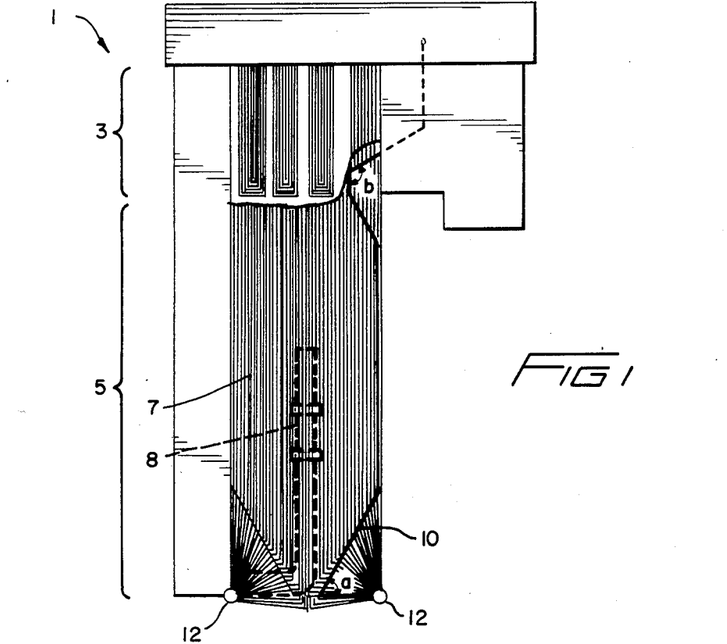

With reference now to FIG. 1, wherein like numerals represent like components of the system throughout all the several figures, the purpose of the invention is to inspect the boiler tubes of a typical fossil fuel steam generator 1. Such steam generators typically include a superheater section 3, and a boiler section 5. The boiler section 5 includes a boiler water wall 7 which surrounds a flame generator 8 and absorbs the heat generated therefrom. The boiler water wall 7 is formed from a relatively densely packed array of zig-zagging boiler tubes 10 which are generally vertically oriented. Water is introduced into each of these tubes 10 and converted to steam which ultimately drives the turbine of an electric generator (not shown).

Figure 2A:
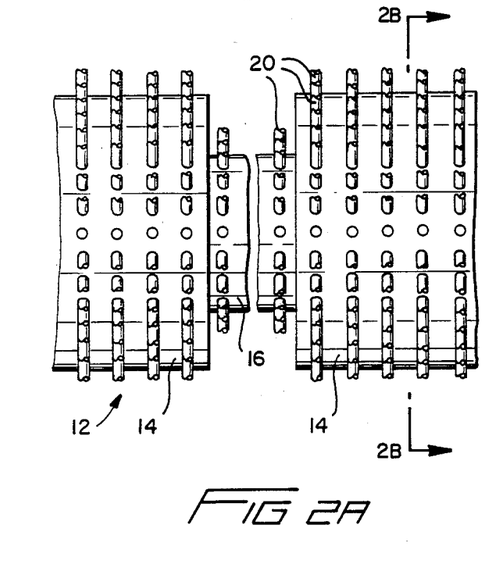
FIG. 2A is a partial side view of one of the mud drums of the steam boiler illustrated in FIG. 1.
Figure 2B:
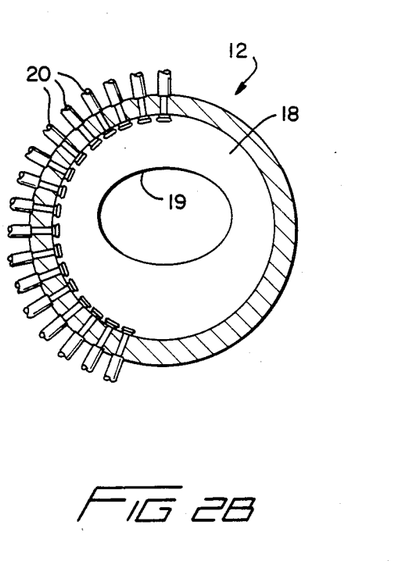
FIG. 2B is a cross-sectional view of the mud drum illustrated in FIG. 2A along the lines 2B—2B.
Figure 3:
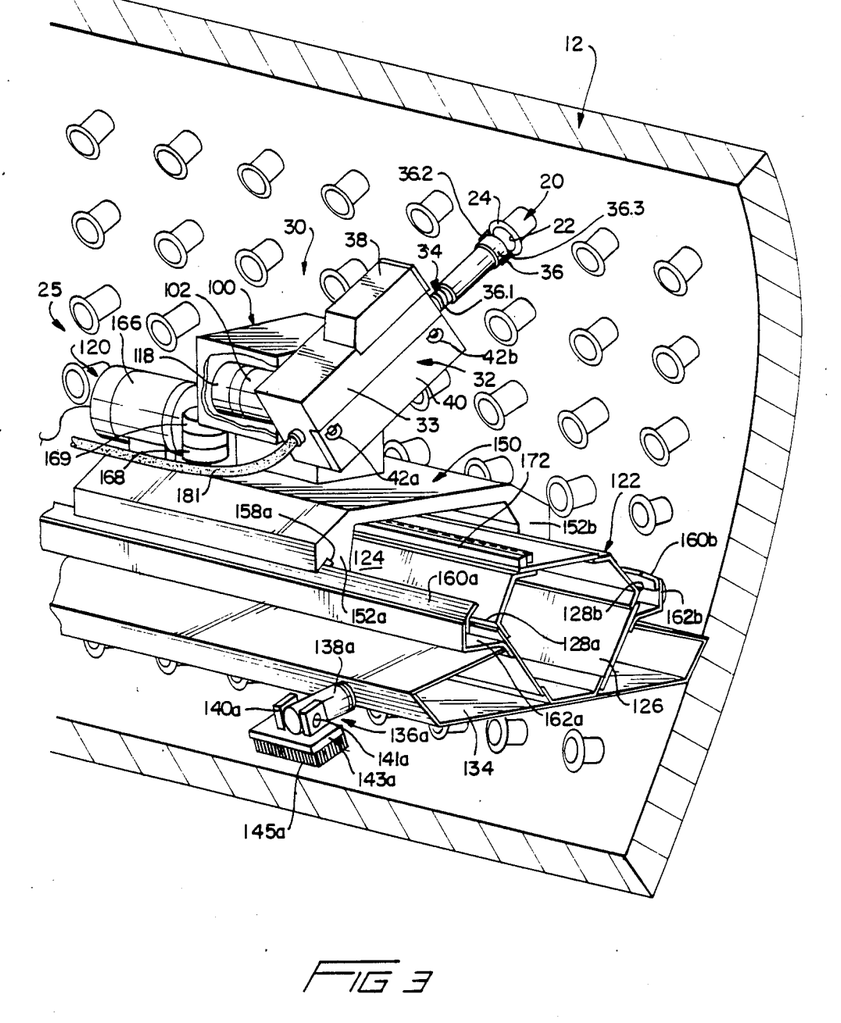
FIG. 3 is a perspective view of the tube inspection system of the invention mounted in one of the mud drums of the boiler.

With reference now to FIGS. 2A and 2B, each of the tubes 10 includes an open end mounted into one of the several mud drums 12 located at the bottom of the generator 1. The mud drums 12 are formed from a plurality of serially connected conduits 14, 16 of wider and narrower diameters which usually range from 14 to 30 inches. Each of the drums 12 is capped by an endplate 18 having an elliptical manway 19. The open ends 20 of each of the tubes 10 are mounted in one of the mud drums 12 in a configuration which roughly resembles a pattern of spokes radiating from a hub. Each of the open ends 20 of the tubes 10 includes a centrally disposed circular opening 22 circumscribed by a flange 24 as shown in FIG. 3. As may be appreciated from FIG. 1, each of the tubes 10 includes one or more 160° turns "a" located a relatively short distance away from its respective mud drum 12. Other turns "b" of about 90° are present at the upper ends of the tubes 10. These relatively sharp turns "a" and "b", in combination with the small diameter of the mud drums 12 throughout much of their lengths render it difficult if not impossible for a human operator to quickly and efficiently snake an eddy current probe throughout each of the tubes 10 in order to inspect their interiors.

Figure 4A:
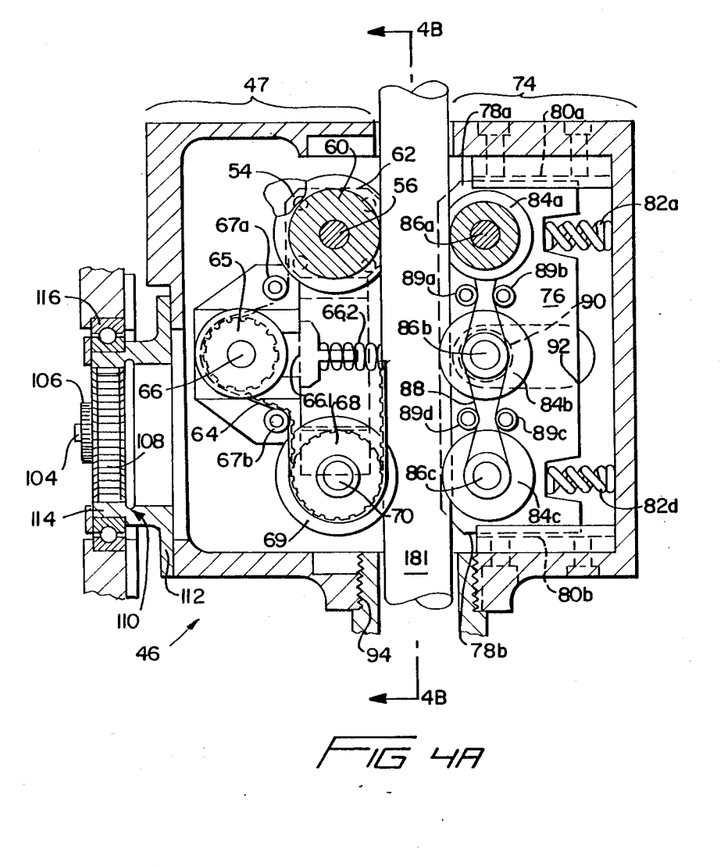
FIG. 4A is a cross-sectional top view of the insertion and pusher drive mechanism of the invention.
Figure 4B:
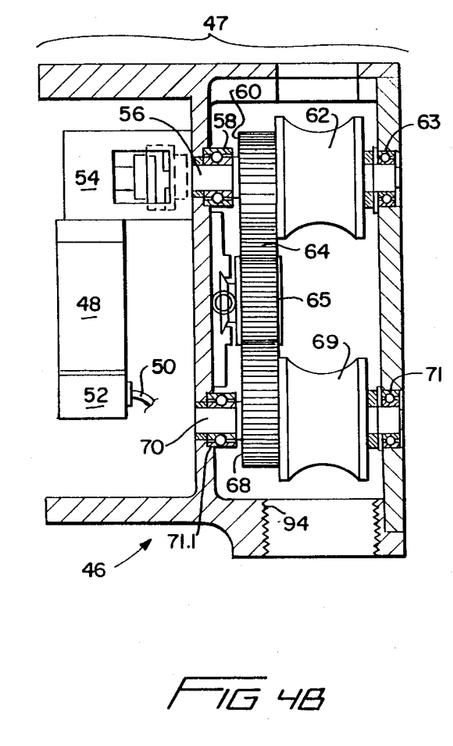
FIG. 4B is a cross-sectional side view of the insertion and pusher drive mechanism illustrated in FIG. 4A along the line 4B—4B.

With reference now to FIGS. 3, 4A and 4B, the tube inspection system 25 of the invention generally comprises a delivery assembly 30 for aligning, inserting and pushing a probe carrier 175 (shown in FIGS. 6A–6E) throughout the entire length of each of the boiler tubes 10. The carrier delivery assembly 30 includes a probe insertion and pusher drive 32 having an extendable and retractable guide tube 34 capable of aligning the generally cylindrical housing of the probe carrier 175 with the circular openings 22 at each of the open ends 20 of the tubes 10. Within the box-like housing 33 of the probe insertion and pusher drive 32 is an insertion and pusher mechanism 46 formed from a pusher drive assembly 47, and a spring-biased pressure idler assembly 74. The pusher drive assembly 47 in turn has a motor 48 for driving a drive gear 60 connected to a drive wheel 62. As will be described in more detail hereinafter, when the access door 40 of the probe insertion and pusher drive 32 is closed, either the probe carrier 175 or its attached pneumatic power cable 181 are captured between the drive wheel 62 and the spring-biased pressure idler assembly 74. The end result is that the probe insertion and pusher drive 32 not only pushes the elongated, cylindrical body of the probe carrrier 175 out through the guide tube 34, but the pneumatic cable 181 as well.

The delivery assembly 30 further includes angular and axial drive mechanisms 100, 120 for rotating the box-like housing 33 of the probe insertion and pusher drive 32 to a desired angle around the circumference of the mud-drum 12, and translating it to a desired point along the longitudinal axis of the mud-drum 12 by means of a carriage 150. The angular and axial drive mechanisms 100, 120 are powered by electric stepping motors 102 and 166, respectively, which are mechanically linked to encoders 118 and 169.

Figures 5A, 5B, 6B, 6E:
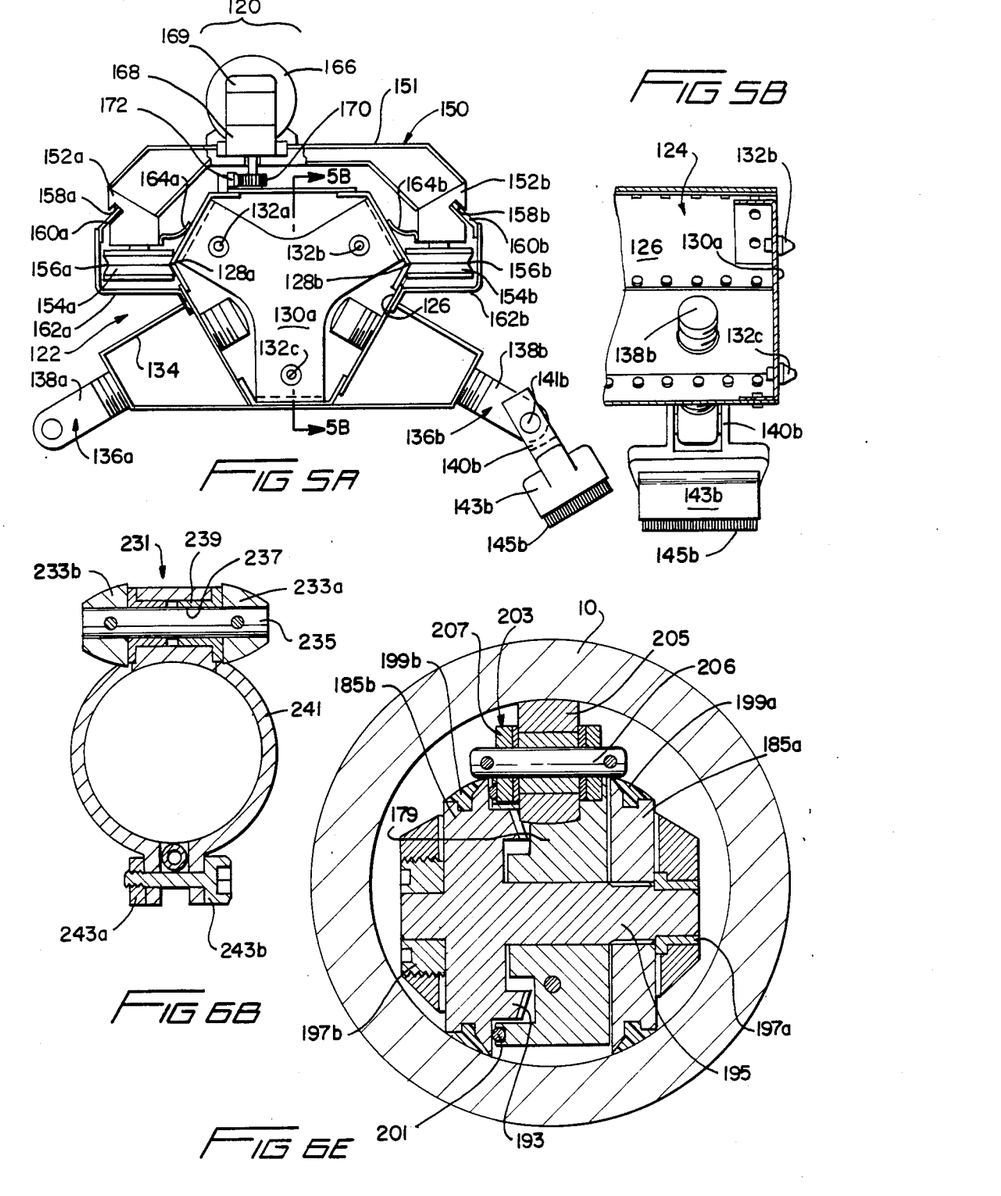
FIG. 5A is a front view of the probe carrier delivery assembly of the invention with the distal member of one of the legs removed.
FIG. 5B is a side, cross-sectional view of the delivery assembly illustrated in FIG. 5A along the line 5B—5B.
FIG. 6B is a cross-sectional view of the probe carrier illustrated in FIG. 6A along the line 6B—6B.
FIG. 6E is a cross-sectional view of the probe carrier illustrated in FIG. 6D along the line 6E—6E.
Figure 6A:
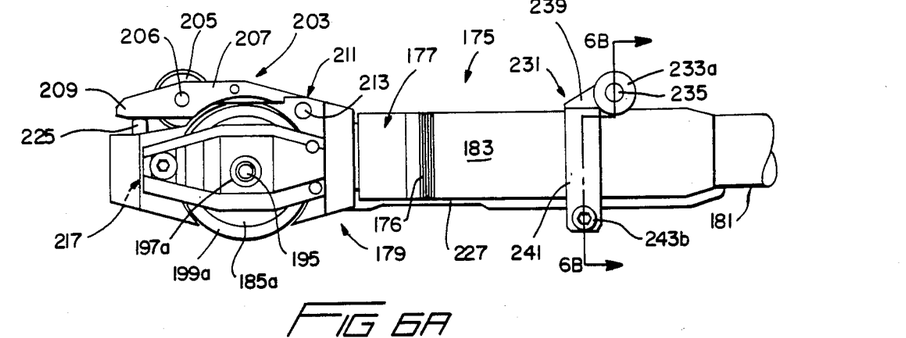
FIG. 6A is a side view of the probe carrier of the invention.
Figure 6C:
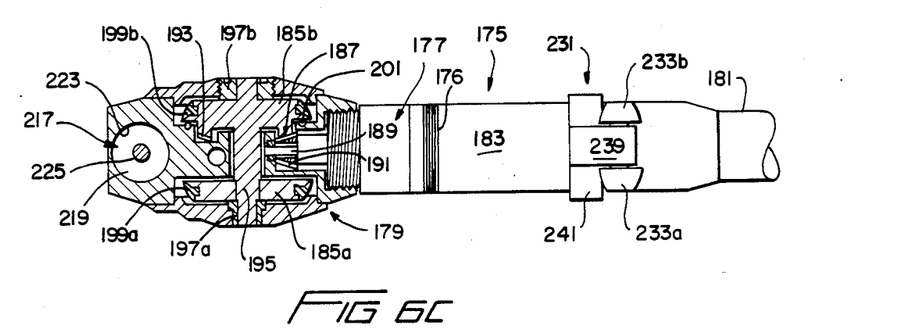
FIGS. 6C and 6D are partial cross-sectional bottom and side views of the probe carrier, respectively.

As is evident from FIGS. 6A, 6B and 6C, the probe carrier 175 drives an eddy current probe 176 through the tubes 10 by means of a drive mechanism 179 which includes a pneumatic motor 184 whose output is engaged to a pair of drive wheels 185a, 185b through a hypoid gear train 187. When this drive mechanism 179 is actuated while the insertion and pusher drive mechanism 46 is pushing the pneumatic power cable 181 behind the probe carrier 175, the probe carrier 175 can easily negotiate the sharp turns "a" and "b" present in each of the boiler tubes 10 of conventional fossil fuel plant 1.

Each time the probe carrier 175 is completely driven through a tube 10, the drive mechanism 179 is deactuated, as is the insertion and pusher drive mechanism 46. The eddy current probe 176 which is carried by the probe carrier 175 is then actuated, while the pneumatic power cable 181 is reeled back toward the delivery assembly 30 by means of the reel assembly 246 illustrated in FIG. 7. The precise location of any damaged sections of the tubes 10 are computed by measuring the amount of pneumatic cable 181 which must be withdrawn to return the probe carrier 175 back to the delivery assembly 30 after an irregularity has been detected by the probe 176.

Figure 8:
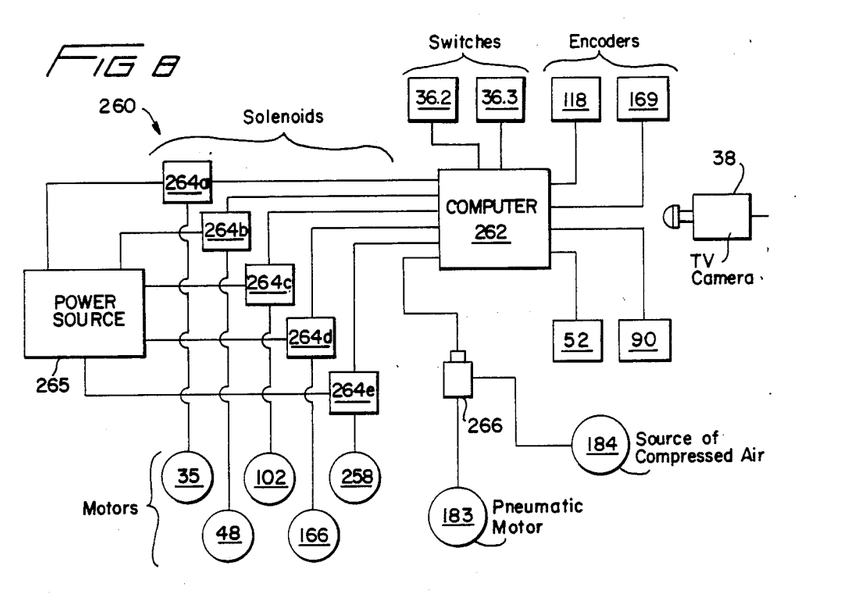
FIG. 8 is a schematic view of the control system of the invention.
Figure 9A:
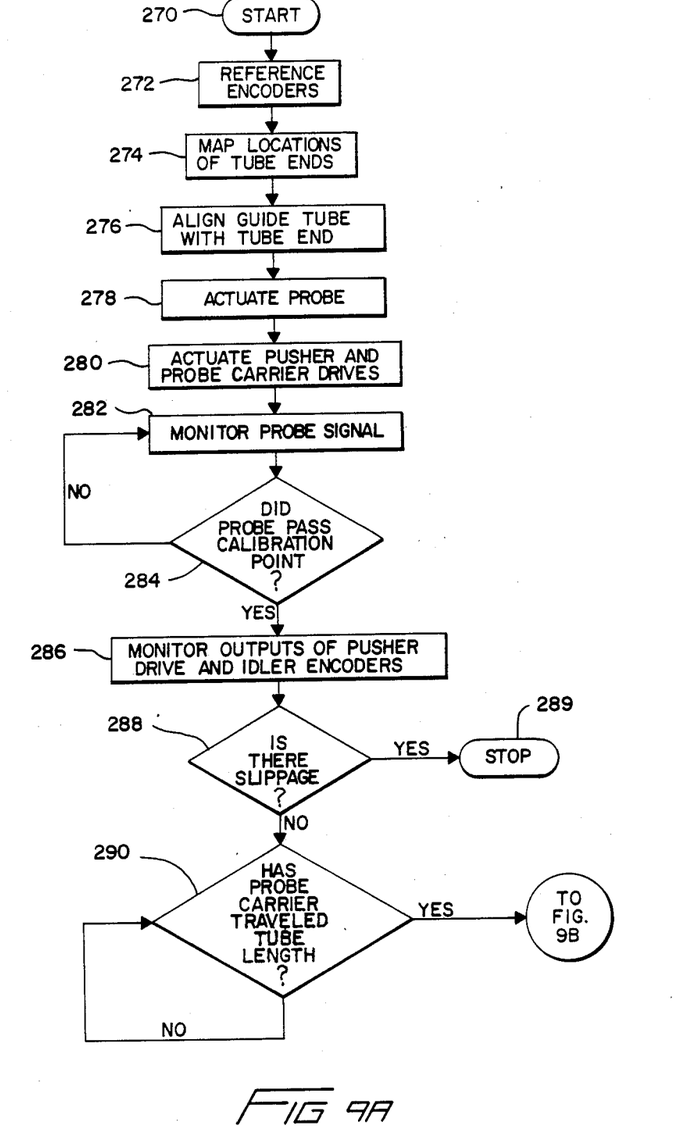
FIGS. 9A and 9B are a flow chart illustrating the operation of the computer in the control system of the invention.
Figure 9B:
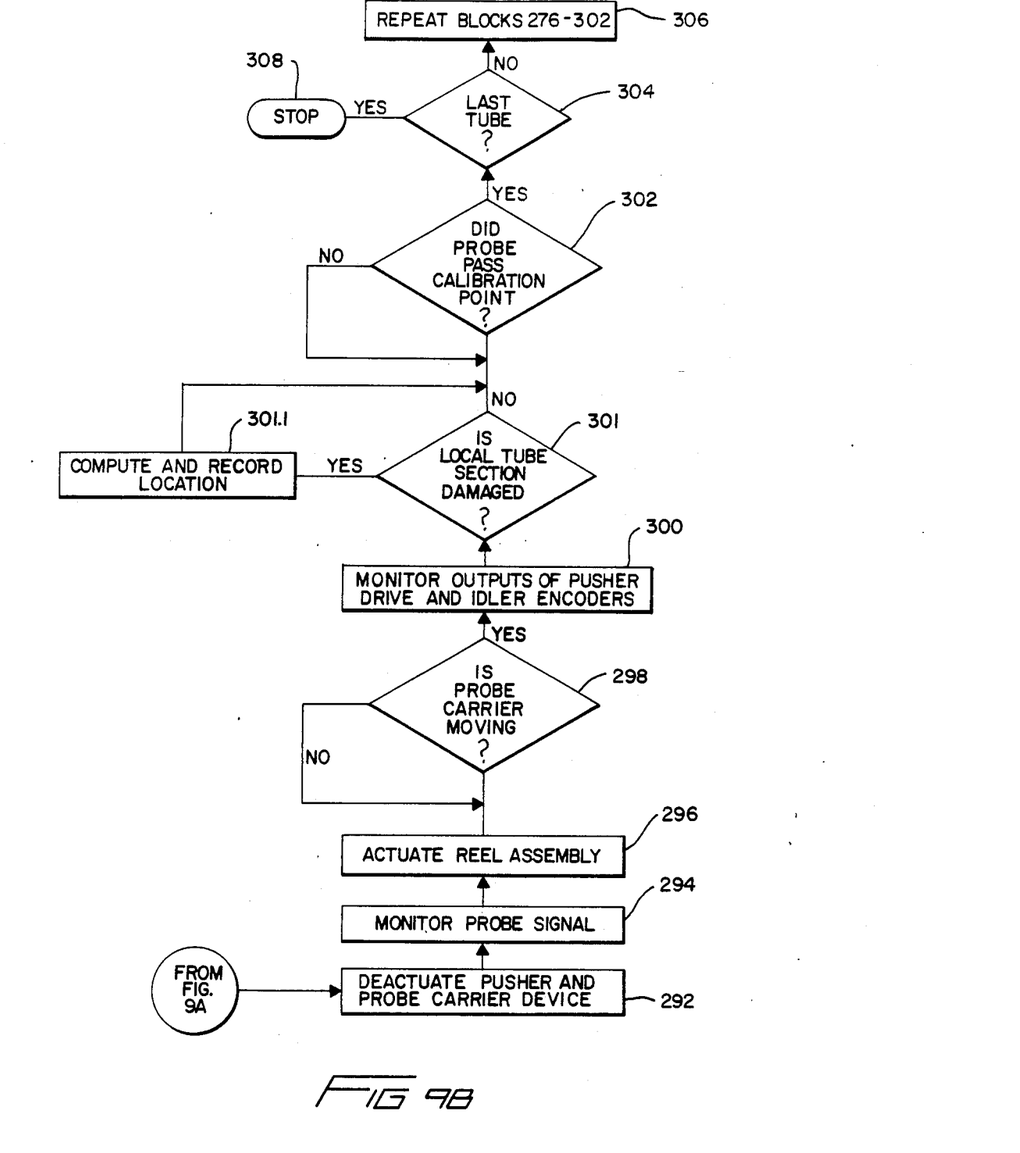

With reference now to FIGS. 8, 9A and 9B, the invention 25 further includes a control system 260 having a television camera 38 and a computer 262. The television camera 38 allows an operator to remotely position the guide tube 34 of the probe insertion and pusher drive 32 into alignment with the open end 20 of a tube 10, while the computer 262 receives encoders 118, 169 which indicate the cylindrical coordinates of the tube 34 whenever the tube 34 is placed into such alignment. The memory capacity of the computer 262 makes it possible to "map" and store the locations of each of the open ends 20 of the tubes 10 prior to the inspection process of the invention. After the location of each of the tube ends 20 has been mapped and stored, the computer 262 automatically inspects each of the tubes 10 in accordance with the program reflected in the flow chart illustrated in FIGS. 9A and 9B by controlling the angular and axial drive motors 102 and 166, as well as the drive mechanism 179 of the probe carrier 175.

Detailed Description of the Structure and Operation of the Invention

With reference now to FIG. 3, the tube inspection system 25 of the invention includes a probe carrier delivery assembly 30 having a probe insertion and pusher drive 32 for both inserting and pushing the probe carrier 175 throughout the length of the tube 10 being inspected. In the preferred embodiment, the probe insertion and pusher drive 32 includes a box-like housing 33 with an extendable and retractable guide tube 34. The guide tube 34 in turn includes a centrally disposed eddy current probe calibrator and guide orifice 36 for both positioning the probe carrier 175 into alignment with the open tube end 20, and detecting when the probe carrier exits or enters the guide tube 34. Although not specifically shown in any of the several figures, the interior of the guide tube 34 has a venturi-like cross-section formed from a ferric alloy. This venturi-shaped profile not only channels the cylindrically shaped probe carrier 175 through a guide orifice which is concentrically aligned with the cylindrical axis of tube 34, but also provides a circular flange of metal which causes the eddy current probe to generate a relatively well-defined spike on the probe readout equipment (not shown) whenever it passes through the narrowest part of the venturi-shaped profile. In the preferred embodiment, the readout equipment is MIZ-12 frequency multiplexer manufactured by ZETEC of Isaquah, Wash.

The eddy current probe calibrator and guide orifice 36 is extended and withdrawn by means of a mechanism very similar in structure to the well-known mechanisms for driving zoom-type lenses. Specifically, the extendable and retractable guide tube 34 includes a spiral groove 36.1 at its proximal portion onto which a pin mounted on a rotable collar (not shown) is engaged. A spur gear (also not shown) circumscribes the rotatably mounted collar. This spur gear is rotated either clockwise or counterclockwise by means of a worm gear driven by a motor 35 (see FIG. 8). To confirm that the tube 34 has been abutted against the open end 20 of a tube 10, a pair of microswitches 36.2 and 36.3 are provided which extend out from the distal edge of the tube 34.

Mounted on top of the box-like housing 33 of the probe insertion and pusher drive 32 is a television camera 38 which includes a light (not shown). Television camera 38 is used to detect the exact extent to which the guide tube 34 is extended or retracted toward the open end 20 of a tube, as well as to control both the angular and axial positioning of the housing 33 for the probe insertion and pusher drive 32, as will be described in detail hereinafter.

With reference now to FIGS. 4A and 4B, the boxlike housing contains an insertion and pusher drive mechanism 46 which is generally comprised of a pusher drive assembly 47, and a pressure idler assembly 74. The pusher drive assembly 47 includes a motor 48 connected to a source of electrical power 265 (see FIG. 8) by way of a power cable 50. An encoder 52 is mechanically engaged to the output shaft of the electric motor 48. The output shaft of the motor 48 is connected to the input of a right angle gear reducer 54. The right angle gear reducer 54 terminates in a drive shaft 56 journalled in a bearing 58 as shown. The drive shaft 56 is concentrically mounted within a drive gear 60 (best seen in FIG. 4A). This drive gear 60 is in turn connected to a drive wheel 62 having an arcuate profile which is preferably complementary in shape to the pneumatic power cable 181 of the probe carrier 175. The drive shaft 56 extends completely through the drive wheel 62, and is journalled in bearing 63 as shown.

Looped around the drive gear 60 is a timing belt 64 having ridges which are complementary in shape to the gear teeth in the gear 60. This timing belt 64 is also looped around an idler gear 65 having teeth of substantially the same shape and distance apart as the teeth of drive gear 60. Idler gear 65 is journalled onto a shaft 66 which in turn is mounted onto a slidable gear mounting 66.1. This gear mounting 66.1 is biased in a direction away from the pressure idler assembly 74 by means of a tensioner spring 66.2. Idler gear 65 is flanked by a pair of idler rollers 67a and 67b as shown. The timing belt 64 loops around the inner sides of each of these idler rollers 67a and 67b, which coact with the tensioner spring 66.2 in maintaining a tight relationship between the timing belt 64, the drive gear 60 and the synchronizer gear 68. The synchronizer gear 68 is mounted onto the synchronizer wheel 69 which is of the same shape and profile as the drive wheel 62. Both the synchronizer gear and wheel 68 and 69 are mounted on a shaft 70 which is in turn journalled on bearings 71 and 71.1. Since both the drive gear 60 and the synchronizer gear 68 are of the same diameter, both the drive wheel 62 and the synchronizer wheel 69 will rotate at the same speed when motor 48 is actuated.

Directly opposite from the pusher drive assembly 47 is the pressure idler assembly 74. The general function of the pressure idler assembly 74 is to bias the probe carrier 175 and pneumatic power cable 181 across the drive and synchronizer wheels 62 and 69 of the pusher drive assembly 47 in order to provide sufficient traction between these wheels and the probe carrier 175 and pneumatic power cable 181 to allow the motor 48 to effectively insert and push the probe carrier 175 through the tubes 10. To this end, the pressure idler assembly 74 includes a mounting plate 76 which is slidably mounted within the box-like housing 33 by dovetail rails 78a and 78b which flank either side of the plate 76, and which are slidably received within complementary dovetail slots 80a and 80b mounted within the housing 33. A pair of compression springs 82a and 82b bias the mounting plate 76 toward the probe carrier 175 and pneumatic power cable 181 during the operation of the invention. In order to minimize the friction between the pressure idler assembly 74 and the probe carrier 175 and cable 181, three idler wheels 84a, 84b and 84c are rotatably mounted along the probe carrier-engaging side of the idler assembly 74. These wheels are rotatably mounted onto wheel shafts 86a, 86b and 86c in a conventional manner, and are all of the same diameter. The motion of each of these wheels is synchronized by means of a synchronizer belt 88 kept tense by four idler rollers 89a, 89b, 89c and 89d, whose inner portions engage the belt 88 in the positions illustrated in FIG. 4A. In order to ensure an accurate readout of the extent to which the motor 48 pushes the probe carrier 175 and pneumatic cable 181 through the tube 10, an absolute encoder 90 is connected to the shaft of the central idler wheel 84b. Slippage between the drive wheel 62 and synchronizer wheel 69 and the probe carrier 175 and pneumatic cable 181 may cause the output of the encoder 52 to be in error; however, idler wheels 84a, 84b and 84c will not rotate unless there is a positive motion of the probe carrier 175 or cable 181 through the guide tube 38. The provision of absolute encoder 90 is particularly useful in determining the extent to which the pneumatic cable 181 is withdrawn. Such information is more important than the extent to which the probe carrier 175 is inserted in the tube, since the eddy current probe on the probe carrier 175 is not actuated until the carrier 175 starts to be withdrawn from the tube 10. In order to assure access to the absolute encoder 90, an oval access port 92 is provided in the slidable mounting plate 76 in the position shown. Also, it should be noted that a quick-connect joint 94 circumscribes the circular opening which receives the probe carrier 175 and cable 181 into the box-like housing 33.

Turning now to FIGS. 3 and 4A, the housing 33 of the probe insertion and pusher drive is connected to probe carrier delivery assembly 30 by means of an angular drive mechanism 100. Angular drive mechanism 100 generally comprises a stepping motor 102 having an output shaft 104 onto which an output gear 106 is connected. This drive gear 106 is received within the recess of a pinion gear 108 (most easily seen in FIG. 4A). Pinion gear 108 is in turn connected to a collar 110. This collar 110 includes a flange portion 112 which is mounted onto the side of the box-like housing 33, and a neck 114 which is journalled within a bearing 116 so that the housing 33 of the probe insertion and pusher drive 32 will rotate whenever the shaft 104 of the stepping motor 102 rotates. In order to monitor the extent to which the stepping motor 102 rotates the housing 33, an angular encoder 118 (shown in FIG. 3) is connected to the output of the motor 102.

As is best seen in FIGS. 3, 5A and 5B, the probe carrier delivery assembly 30 further includes an axial drive mechanism 120 for translating both the probe insertion and pusher drive 32 and angular drive mechanism 100 to a desired point along the longitudinal axis of a mud drum 12. This axial drive mechanism 120 includes a rail assembly 122 formed from a plurality of rail members 124 detachably connected to one another in tandem. Each of these rail members 124 includes a hexagonal support frame 126 whose horizontal opposing edges define rail surfaces 128a and 128b. Each of the rail members 124 further includes front and rear plates 130a, 130b (of which only 130a is visible). The front plates 130a each include a triangular array of alignment pins 132a, 132b and 132c, while the rear plate 130b includes a triangular array of dimples (not shown) which are complementary in shape to the alignment pins 132a, 132b, and 132c. The provision of such alignment pins 132a, 132b, and 132c and complementary dimples in the front and rear plates 130a, 130b allows the rail members 124 to be conveniently and accurately mounted in tandem to form a substantially straight rail assembly 122.

At the bottom of each of the hexagonal support frames 126 of the rail members 124 a leg support 134 is provided. This leg support 134 includes a pair of threaded bores on either side for receiving the upper portion of four adjustable legs 136a–136d. Each of these adjustable legs 136a–136d includes a threaded proximal member 138 which may be screwed into one of the four bores of the leg support 134. Additionally, each of the legs 136a–136d includes a distal leg member 140, as well as a pivot joint 141 for pivotably connecting the proximal and distal leg members 138 and 140. Each of the distal leg members 140 further includes a foot 143 which terminates in an electromagnet 145. Since the mud drums 12 are generally formed from carbon steel (or some other magnetic alloy), the provision of an electromagnet 145 on the feet 143 of the legs allows the legs to be detachably mounted on the inner surface of the mud drum 12. Additionally, the provision of a threaded region on the proximal leg members 138 allows the length of the legs 136a–136d to be adjusted. This is important, since the inner diameters of the mud drums 12 change throughout their lengths due to the fact that each of the mud drums 12 is formed from cylindrical conduit sections 14, 16 having smaller and larger diameters, respectively.

With reference now to FIGS. 3 and 5A, the probe carrier delivery assembly 30 also includes a carriage 150 which is translatable along the longitudinal axis of the rail assembly formed by the rail members. Generally, the carriage 150 includes a flat, rectangular bed 151 having a pair of opposing wheel support brackets 152a, 152b on either side. Each of the wheel brackets 152a, 152b includes a pair of carriage wheels 154a, 154b and 154c, 154d, respectively, of which only 154a and 154b are visible. Each of the carriage wheels 154a–154d is recessed along its periphery by a V-shaped groove 156 which is complementary to the V-shape of the rail surfaces 128a, 128b of the rail members 124.

To prevent rust, scale, soot or other debris from falling in between the V-shaped grooves 156 of the carriage wheels 154a–154d and the rail surfaces 128a, 128b, outer scale guards 160a and 160b are provided.

Each of the opposing support brackets 152a, 152b further includes a slot 158a, 158b for receiving an outer scale guard 160a, 160b which is mounted along the midportion of the hexagonal support frame 126 by means of scale guard brackets 162a, 162b. Additional inner scale guards 164a, 164b are also mounted along the interior surfaces of the opposing brackets 152a, 152b to further prevent scale from entering this space. Both the outer and inner scale guards 160a, 160b and 164a, 164b are preferably formed from a tough, resilient material, such as rubber or polyurethane.

In order to selectively drive the carriage 150 to a desired point along the longitudinal axis of the rail assembly 122, an axial drive motor 166 is provided on top of the flat, rectangular bed 151. The output shaft of this axial drive motor 166 is connected to a right-angle gearbox 168 which is further connected to an encoder 169. The output shaft of the right-angle gearbox 168 is in turn connected to a pinion gear which engages a rack 172. This rack 172 is mounted in parallel relationship with the longitudinal axis of the rail members 124. The axial encoder 169 provides an accurate indication of the extent to which the axial drive motor 166 has moved the carriage 150 along the rail assembly 122.

With reference now to FIGS. 6A, 6B, and 6C, the probe carrier 175 of the invention includes both an eddy current probe 176 and a drive mechanism 179. The eddy current probe 176 circumscribes the elongated housing 177 of the carrier 175 in the position shown. The drive mechanism 179 is generally formed from a pneumatic motor 183 which powers a pair of drive wheels 185a, 185b through a hypoid gear train 187. This pneumatic motor 183 is powered by the previously mentioned pneumatic power cable 181 which in turn is connected to a source of pneumatic power 184 (schematically represented in FIG. 8). The use of a pneumatic motor 183 is preferred over an electric motor because such a motor is capable of generating a much greater output of power than an electric motor of comparable dimensions and weight could without radiating magnetic field fluxes which could interfere with the accurate operation of the eddy current probe 176. The use of a hypoid gear train 187 is likewise preferred due to the superior ability of this particular drive train configuration to efficiently and quietly transmit mechanical power.

The distal end of the pneumatic motor 183 (from the operator's perspective) terminates in an output shaft 189. Connected to this shaft 189 is a hypoid output gear 191 whose teeth mesh with a hypoid drive gear 193 mounted around the inside surface of drive wheel 185b. An axle connects the drive wheels 185a, 185b so that wheel 185a is driven along with wheel 185b. The ends of the axle 195 are journalled within bearings 197a, 197b as indicated. Bearing 197b is threaded along its outer circumference in order to render it easily removable in the event that it become necessary to disassemble the probe carrier 175. Each of the drive wheels 185a, 185b is circumscribed by a polyurethane tire 199a, 199b. The tires 199a, 199b enhance the traction of the drive wheels 185a, 185b along the inside surface of the tubes 10, and also prevent the outer edges of the wheels 185a, 185b from wearing down. In order to maintain proper engagement between the output gear 191 and the drive gear 193 forming the hypoid gear train 187, a sealing ring 201 abuts the inner surface of the drive wheel 185b in the position shown. The provision of such a sealing bearing ring 201 prevents scale and dirt from entering into the gear train.

Figure 6D:
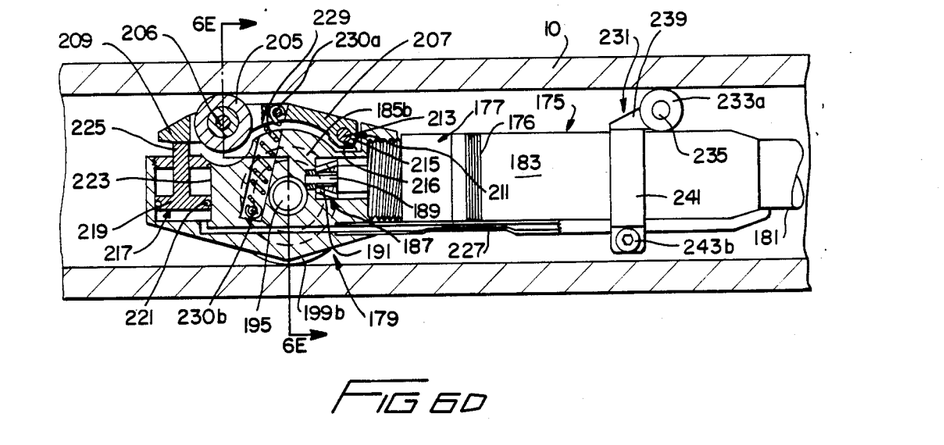

With reference now to FIGS. 6D and 6E, the probe carrier 175 further includes a load wheel assembly 203 disposed 180° opposite from the drive mechanism 179. The load wheel assembly 203 ensures that there is always sufficient traction between the drive wheels 185a, 185b and the inner surface of the conduits 10 to allow the probe carrier 175 to be driven by the drive mechanism 179. The load wheel assembly 203 includes a single load wheel 205 which is journalled on an axle 206. Axle 206 is mounted on a pivotable arm 207 connected to the elongated housing 177 of the probe carrier 175. The pivotable arm 207 includes a tapered portion on its front end which helps prevent the load wheel assembly 203 from snagging on the scaly interior of the conduits 10, as well as a pivot joint 211 on its rear end for allowing the wheel 205 to be extended and retracted relative to the radius of the tube 10. The pivot joint 211 is formed from a pin which pivotably mounts the generally rectangular, rear corner of the arm 207 within a complementary recess 216 in the housing 177 of the probe carrier 175.

A pneumatic cylinder 217 is mounted in the front part of the probe carrier 175 for both radially extending the load wheel 205 into engagement with the inner wall of a tube 10 and for resiliently maintaining the load wheel 205 in such engagement. The radial extension and biasing of the load wheel 205 in this position ensures that the polyurethane tires 199a, 199b will stay in traction-producing engagement against the inner walls of the tube 10. As is best seen in FIG. 6D, the pneumatic cylinder 217 includes a piston 219 circumscribed by a sealing ring 221 which reciprocates in a cylinder 223 whose cylindrical axis is radially disposed with respect to the longitudinal axis of the probe carrier 175. A push rod 225 connected to the piston 219 abuts the underside of the front tapered end 209 of the pivotable arm 207 of the load wheel assembly 203. A pneumatic air line 227 connected to the bottom portion of the pneumatic cylinder 217 connects this cylinder to the source of compressed air 184 via line 181 as shown. In order to ensure that the pivotable arm 207 will retract toward the body of the probe carrier 175 when the push rod 225 of the pneumatic cylinder 217 is withdrawn, a retraction spring 229 is provided. This retraction spring 229 is looped at either end around pins 230a, 230b connected to the pivotable arm 207, and a front centrally disposed section of the elongated housing 177 of the probe carrier 175, respectively. The inwardly directed tension that the retraction spring 229 exerts on the pivotably mounted rod 207 ensures that the load wheel 205 will radially withdraw whenever the bottom portion of the pneumatic cylinder 217 is relieved of compressed air from the pneumatic power line 181 via line 227 which is fluidly connected thereto.

With reference now to FIGS. 6A, 6B and 6C, the probe carrier 175 further includes a guide wheel assembly 231 for preventing the rear portion of the body 177 of the probe carrier 175 from frictionally engaging the interior wall of the tube 10 as the probe carrier 175 travels along the longitudinal axis of the tube. This guide wheel assembly 231 includes a pair of rotatably mounted guide wheels 233a, 233b rigidly connected together by means of an axle 235. This axle 235 is in turn journalled within a bore 237 in a wheel bracket 239. A clamp 241 is provided for securing the wheel bracket 239 around the substantially cylindrical housing 117 of the probe carrier 175. In the preferred embodiment, this clamp is fastened around the cylindrical body 177 of the probe carrier 175 by a conventional nut and bolt arrangement 243.

The guide wheels 233a, 233b are preferably located on the same side of the cylindrical housing 177 as the load wheel 205. The reason for such an alignment is best understood with reference to FIG. 6D. As is evident from this figure, the axis of rotation of the load wheel 205 is positioned a short distance in front of the axis of rotation of the drive wheels 185a, 185b of the drive mechanism 182. Accordingly, when the load wheel 205 is radially extended by means of the push rod 225 of the pneumatic cylinder 217, the rear or proximal end of the cylindrical body 177 of the probe carrier 175 will experience a significant amount of angular force as the load wheel 205 and the drive wheels 185a, 185d simultaneously engage the inner walls of the tube 10. However, when the rear of the substantially cylindrical body 177 of the probe carrier 175 pivots upwardly in response to this angular force, the probe carrier 175 wil assume the position illustrated in FIG. 6D, wherein the guide wheels 233 engage the inner walls of the tube 10 and prevent any portion of the cylindrical body 177 of the probe carrier 175 from scraping against these walls as the probe carrier 175 travels through them.

If desired, an ultrasonic probe may be used in lieu of an eddy current probe. Further, the pneumatic motor 183, hypoid gear train 187, and the motor 48 and right angle gear reducer 54 of the pusher drive assembly 47 should be chosen so that the probe carrier is both pulled and pushed through the tubes 10 at a speed of about 12 inches per second.

Figure 7:
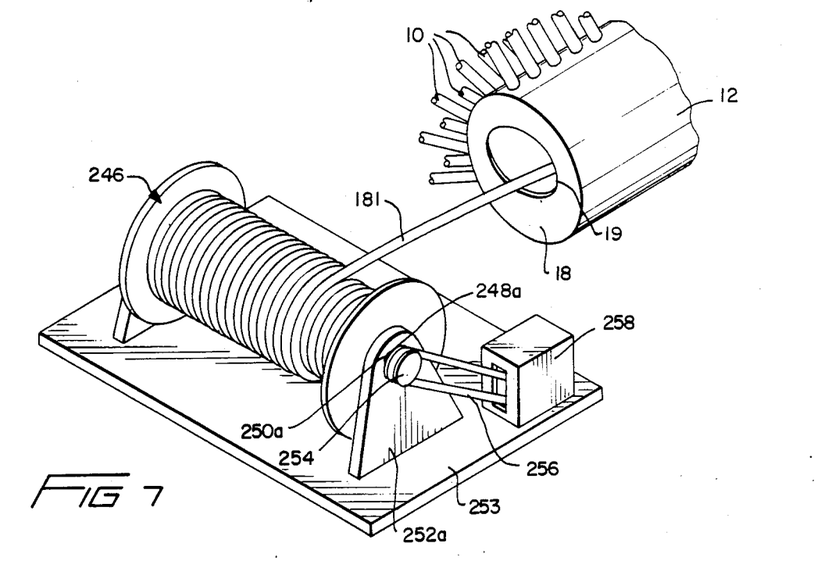
FIG. 7 is a perspective view of the reel drive of the delivery assembly of the invention.

Turning now to FIG. 7, a reel assembly 246 is provided for withdrawing the probe carrier 175 back to the delivery assembly 30 after the pusher drive assembly 47 of the insertion and pusher drive mechanism 46 and the drive mechanism 179 have simultaneously pushed and pulled the probe carrier 175 completely through a tube 10 prior to its inspection. The reel assembly 246 comprises a reel as shown having a pair of stub shafts 248a, 248b which extend from either end, of which only shaft 248a is visible. These stub shafts 248a, 248b are journalled within bores 250a, 250b present at the upper ends of a pair of mounting flanges 252a, 252b which in turn are secured at their bottom portions on a platform 253, of which only bores 250a and flange 252a are visible. A simple pulley 254 mounted on the end of the stub shaft 248a is engaged to a reel-winding motor 258 by means of a belt 256. The reel-winding motor 258 may be any one of a number of commercially available stepping-electric motor and drive-train combinations. As may be seen in FIG. 8, the electric motor 258 is connected to a power source 265 by way of a solenoid 264e for a purpose which will be explained shortly. As is evident from FIG. 7, the reel assembly 246 is capable of withdrawing the probe carrier 175 along the interior of a tube 10 by reeling up the pneumatic power line 181 connected to the rear of the carrier 175. In the preferred embodiment, the pneumatic power line 181 extends through the elliptical manway 19 of the endplate 18 of a mud drum 12 in order to minimize the chances of the pneumatic power line 181 binding against the walls or the tube ends 20 of the mud drum 12.

FIG. 8 is a schematic representation of the control system 260 of the invention. Generally, the control system 260 includes the previously described television camera 38 having its own light source, and a computer 262. On its output side, the computer 262 is connected to the microswitches 36.2 and 36.3, the pusher drive assembly encoder 52, the absolute or idler encoder 90, the angular encoder 118, and the axial encoder 169. On its output side, the computer 262 is connected to a plurality of electrically operated switches or relays 264a, 264b, 264c, 264d, 264e and 264f. The relays 264a–264f connect and disconnect the guide tube extension and retraction motor 35, the pusher drive assembly motor 48, the angular drive motor 102, the axial drive motor 166, and the reel assembly motor 258. The output of computer 262 is further connected to an electrically controlled pneumatic valve 266 which connects and disconnects the previously mentioned pneumatic motor 183 (and the pneumatic cylinder 217 of the load wheel assembly 203) of the probe carrier assembly 175 from a source 184 of compressed air. In the preferred embodiment, the encoders 52, 90, 118 and 169 may each be a DS series encoder manufactured by Computer Conversions Corp. located in Northport, N.Y. Moreover, the computer 262 is preferably a Model 9836 computer manufactured by Hewlett-Packard Corp. located in San Jose, Calif. The electrically operated switches 264a–264e may each be a Model 6HM1-1 switch manufactured by Micro Switch located in Freeport, Ill. Finally, the power source 265 is preferably a pulsed, DC power source in order that the precise angular rotation of the stepping motors 35, 48, 102, 166, and 258 may be selectively controlled.

Both the process of the invention and the operation of the tube inspection system 25 may best be understood with respect to the flowchart illustrated in FIGS. 9A and 9B which represents a generalized description of the software utilized in connection with the computer 262. This program is implemented after the rail members 124 of the rail assembly 122 have been installed in tandem by adjusting the length of the adjustable legs 136a–136d with respect to the leg support 134 of each of the members 124.

After the computer 262 is started at block 270, it immediately begins to index the angular and axial encoders 118 and 169 by locating "zero" position reference points in order that the precise location of each of the open tube ends 20 in the mud drum 12 may be unambiguously mapped. The computer 262 achieves a "zero" angular reference point by commanding the angular drive motor 102 to rotate the box-like housing 33 of the probe carrier delivery assembly 30 until a mercury-filled switch (not shown) indicates that the extendable and retractable guide tube 34 extending out of the housing 33 is approximately level with respect to the horizontal. When such orientation is achieved, the computer 262 deactuates the angular drive motor 102, and considers the orientation of the extendable and retractable guide tube to be at zero degrees with respect to the horizontal. At the same time the computer 262 is issuing such commands to the angular drive motor 102, it also actuates the axial drive motor 166 so that it drives the carriage 150 to the maximum extend possible along the rail assembly 122. When the carriage 150 strikes a microswitch (not shown) located at the end of the rail assembly 122, the computer 262 immediately disconnects the axial drive motor 166 from the power source 265 by changing the state of solenoid 261, and considers this position of the carriage 150 as the "zero" axial position.

In the next block 274 of the program of the computer 262, the tube inspection system proceeds to "map" and store the positions of each of the open ends of the tubes 20. This "mapping" step of the process is accomplished in part by a human operator who remotely moves the extendable and retractable guide tube 34 with each of the open ends of the tubes 20 by visually monitoring the position of the extendable and retractable guide tube 34 by means of the TV camera 38, and by deactuating the angular and axial drive motors 102 and 166 by commanding the motor 262 to change the states of the electrically operated switches 264c and 264d when alignment is obtained. For each tube, when alignment is obtained, the operator then instructs the computer 262 to store the cylindrical coordinates relative to the "zero" position angular and axial reference points which the computer 262 located back at block 272.

After the location of each of the open tube ends 20 has been mapped, the operator commands the computer to carry out the probe carrier positioning subroutine contained in blocks 276 through 292. After this subroutine is actuated, the computer 262 proceeds to block 276, and aligns the guide tube 34 with the first open end 20 mapped in the course of the mapping step 274. The computer automatically actuates the eddy current probe 176 which circumscribes the probe carrier 175, as is indicated in block 278. Next, it proceeds to block 280, and simultaneously actuates both the pusher drive assembly 47 of the insertion and pusher drive mechanism 46 and the drive mechanism 179 of the probe carrier 175, so that the probe carrier 175 is simultaneously pushed and pulled through the extendable and retractable guide tube 34 and into the open tube end 20.

Next, as is indicated by block 282, the signal generated by the eddy current probe 176 is monitored in order to determine whether or not the probe 176 has passed the calibrator 36 located within the guide tube 34. As is indicated in question block 284, the computer 262 constantly asks the question of whether or note the probe passed the calibrator 36 until it obtains an affirmative answer, whereupon it proceeds to block 286.

At block 286, computer 262 begins to monitor the outputs of the pusher drive and idler encoders 52 and 90 in order to determine (1) whether or not slippage is occuring between the pneumatic power line 181 and the drive and synchronization wheel 62, 69 of the pusher drive assembly 47, as well as (2) whether or not the probe carrier 175 has traveled the length of the tube 10 being inspected. The computer determines the answer to the slippage question (schematically represented in question block 288) by comparing the outputs of the pusher drive and absolute encoders 52 and 90. When no slippage is occurring, the outputs of both of these encoders are virtually identical; however, when the drive wheel 62 and synchronizer wheel 69 rotate without producing a corresponding axial motion in the pneumatic power line 181, the output of the encoder 90 of the pressure idler assembly 74 will be zero., Under such conditions, the computer 262 will deactuate the pusher drive motor 48 by changing the state of the electrical switch 264d, as is indicated by "stop" block 289. However, if no slippage is detected, the computer 262 will proceed to question block 290, and ask whether or not the probe carrier 175 has traveled substantially the entire length of the tube 10 being inspected. It determines the answer to this question by counting the pulses generated by the pressure idler assembly encoder 90, and converting the pulses received therefrom into a distance, and comparing this distance to a preselected distance entered into the memory of the computer 262. As soon as the computer 262 finds that the actual distance equals the preselected distance, it proceeds to block 292 and deactuates both the motor 48 of the pusher drive assembly 47 and the drive mechanism 179 of the probe carrier 175, by changing the states of solenoid 264b and electrically operated valve 266.

After the pusher drive assembly 47 and the drive mechanism 179 of the probe carrier 175 have been deactuated, the computer 262 then proceeds to blocks 294 and 296 and begins to monitor the signal generated by the eddy current probe 176 at the same time as it actuates the reel assembly 246. Because the pneumatic power line 181 "bunches up" to a certain extent as it is being simultaneously pushed and pulled along a tube 10 by the pusher drive assembly 47 and the probe carrier 175, there will be a certain amount of slack in this line at this juncture in the process. It is necessary for this slack in the pneumatic power line 181 to be removed if damaged portions of the tubes 10 are to be located accurately. Consequently, the computer 262 repeatedly asks the question in block 298 ("Is probe carrier moving?"), and notes the point in time when the signal from the eddy current probe 176 indicates that all of this slack has been removed, and that the probe carrier 175 has begun to be withdrawn through the tube 10 by the reel assembly 246.

As soon as such movement is detected, the computer 262 proceeds to block 300 and begins to monitor the output of the idler assembly encoder 90. After such monitoring commences, the computer 262 can ascribe a specific longitudinal distance along the axis of a tube 10 being inspected with each pulse generated by the idler encoder 90. Whenever the eddy current probe 175 generates a signal indicative of a damaged condition in the wall of the tube 10, the computer 262 automatically computes the location of this damaged portion of the tube 10 by noting the number of pulses which have been generated by the idler of absolute encoder 90 since all of the slack was removed from the pneumatic line 181.

The computer 262 continues to reel the probe carrier 175 in toward the probe insertion and pusher drive 32 until the answer to the inquiry in question block 302 ("Did probe pass calibration point?") is answered in the affirmative. Such an affirmative answer will take place when the eddy current probe 176 again passes the calibrator 36 present in the guide tube 34. As soon as this occurs, the computer 262 then proceeds to question block 304, and asks whether or not the tube 10 which was inspected was the last tube mapped. If the answer to this inquiry is negative, the computer proceeds to block 306, and repeats blocks 276–302, which results in the inspection of another tube 10. However, if the answer to this inquiry is affirmative, the computer 262 proceeds to block 308 and stops the program.

What is claimed is:

1. An inspection system for inspecting a plurality of conduits, each of which includes one or more bends, and each of which has an open end mounted in a manifold, comprising:
   (a) a probe carrier having a housing insertable within the open ends of said conduit that contains both a probe for inspecting the condition of said conduits and a drive means for pullingly driving the carrier along the longitudinal axis of said conduits substantially along their entire lengths, wherein a flexible member is connected to said probe carrier, and
   (b) a delivery assembly installable within said manifold for remotely delivering said probe carrier into the open end of a selected one of said conduits including an insertion and pusher means engaged to said flexible member for both inserting the probe carrier into said open end, and assisting the drive means of the probe carrier in driving the carrier along the longitudinal axis of the conduit through said bend by simultaneously pushing the flexible member of the probe carrier as the drive means pullingly drives the probe carrier into the open end of the tube and substantially throughout the length of the tube.

2. An inspection system as defined in claim 1, wherein said flexible member connected to said probe carrier is a flexible cable.

3. An inspection system as defined in claim 1, wherein the drive means of the probe carrier includes at least one drive wheel that yieldably engages the inner surface of the conduit for pulling the carrier along the longitudinal axis of the conduit.

4. An inspection system as defined in claim 1, wherein said carrier delivery assembly includes an angular drive means operatively connected to said insertion and pusher means for rotating the insertion means to a selected angle around the longitudinal axis of the manifold, and an axial drive means for moving the insertion and pusher means to a selected point along the longitudinal axis of the manifold.

5. An inspection system as defined in claim 4, wherein said axial drive means includes a rail assembly which is removably mountable within said manifold, and a carriage slidably mounted on said rail assembly for supporting and axially positioning said insertion means and pusher.

6. An inspection system as defined in claim 1, wherein said drive means of the probe carrier includes a pneumatic motor.

7. An inspection system as defined in claim 6, wherein said drive means of the probe carrier further includes at least one drive wheel connected to said motor for driving the carrier through the conduit.

8. An inspection system as defined in claim 1, wherein said conduits are metallic, and said probe carrier includes an eddy current probe for detecting faults in said conduits.

9. An inspection system as defined in claim 4, further including a control system having a visual monitoring means for visually guiding the insertion and pusher means into alignment with a selected one of the open ends of said conduits.

10. An inspection system as defined in claim 1, wherein said insertion and pusher means includes an extendable and retractable guide tube for guiding the probe carrier into alignment with the open end of a selected conduit.

11. An inspection system as defined in claim 10, wherein said guide tube includes a calibration standard for calibrating the eddy current probe in the probe carrier whenever it moves through the guide tube.

12. An inspection system as defined in claim 9, wherein said control system further includes a computer circuit, and first and second encoder means operatively connected to said angular and axial drive means, respectively, and electrically connected to said computer circuit for generating electrical signals indicative of the position of the angular drive means and the axial drive means with respect to the manifold.

13. An inspection system as defined in claim 7, wherein said drive means of the probe carrier further includes a hypoid gear train for connecting said drive wheel to the output of the pneumatic motor.

14. An inspection system as defined in claim 1, wherein said drive means includes at least one drive wheel for driving the probe carrier along the longitudinal axis of the conduit, and means for biasing said drive wheel against the inner surface of said conduit into driving engagement.

15. An inspection system as defined in claim 14, wherein said biasing means exerts a biasing force sufficient to position said wheel into driving engagement against the inner surface of the conduit regardless of the vertical orientation of the conduit, or the probe carrier within the conduit.

16. An inspection system as defined in claim 14, wherein said biasing means is selectively operable.

17. An inspection system as defined in claim 14, wherein said biasing means is a load wheel assembly which includes at least one radially extendable load wheel rotatably mounted on the opposite side of the drive wheel for biasing said drive wheel against the inner surface of the conduit.

18. An inspection system as defined in claim 17, wherein said load wheel assembly further includes a hydraulically operated piston for both selectively radially extending said load wheel against the inner surface of the conduit so that the drive wheel is engaged against the inner surface of the conduit, and for resiliently biasing said drive wheel against the inner surface of the conduit.

19. An inspection system for sequentially inspecting a plurality of tubes, each of which has an open end mounted in a manifold and some of which include one or more bends, comprising:
  (a) a probe carrier having a housing insertable within the open ends of said tubes that contains both a probe for sensing the condition of said tubes, and a drive means including at least one drive wheel that yieldably engages the inner surface of the tube for pullingly driving the carrier along the longitudinal axis of said tube,
  (b) a flexible member connected to said housing, and
  (c) a delivery assembly removably mountable within said manifold for remotely delivering said probe carrier into the open end of a selected one of said tubes including an insertion and pusher means engaged to said flexible member for inserting the probe carrier into said open end, and assisting the drive means of the probe carrier in negotiating bends in the tubes by simultaneously pushing the flexible member of the probe carrier throughout the length of the tube as said drive means pullingly drives said probe carrier along the length of the tube.

20. An inspection system as defined in claim 19, wherein said flexible member connected to the housing of the probe carrier is a flexible power cable.

21. An inspection system as defined in claim 19, wherein said delivery assembly includes an angular drive means connected to said insertion and pusher means for rotating the insertion and pusher means to a selected angle around the longitudinal axis of the manifold, and an axial drive means for moving the insertion and pusher means to a selected point along the longitudinal axis of the manifold.

22. An inspection system as defined in claim 21, further including a control system having both a visual monitoring means for visually guiding said insertion and pusher means into alignment with a selected one of said open tube ends, and a mapping means for noting and storing both the angle around and point along the longitudinal axis that the insertion and pusher means assumed when aligning the probe carrier with the open ends of the tube so that the cylindrical coordinates of each tube inspected may be recorded.

23. An inspection system as defined in claim 22, wherein said mapping means includes an angular distance encoder operatively connected to said angular drive means, a longitudinal distance encoder operatively connected to said axial drive means, and a computer circuit electrically connected to said encoders for computing and recording the cylindrical coordinates of each tube open end.

24. An inspection system as defined in claim 23, wherein said angular and axial drive means each includes an electrical stepping motor which is connected to a source of power, which is regulated by the computer circuit.

25. An inspection system as defined in claim 19, wherein said insertion and pusher means includes an extendable and retractable guide tube for guiding the probe carrier into alignment with the open end of a selected tube.

26. An inspection system as defined in claim 25, wherein said guide tube includes a calibration standard for calibrating an eddy current probe mounted on the probe carrier.

27. An inspection system as defined in claim 21, further including means for withdrawing the probe carrier from the tube, including a reeling means connected to the flexible member.

28. An inspection system as defined in claim 27, wherein said axial drive means includes a rail assembly which is removably mountable within said manifold, and a carriage slidably mounted on said rail assembly for supporting and axially positioning said insertion and pusher means.

29. An inspection system as defined in claim 28, wherein said rail assembly includes a plurality of elongated rail members which are detachably connected to one another in tandem.

30. An inspection system as defined in claim 29, wherein each of the elongated rail members includes at least two leg means of adjustable length for mounting said rail member along the longitudinal axis of the manifold.

31. An inspection system as defined in claim 30, wherein each leg means includes an electromagnet for detachably mounting its respective rail member within the manifold.

32. An inspection system as defined in claim 19, further including a control system having a computer, and first and second encoder means operatively connected to said drive means of the probe carrier and to said insertion and pusher means, respectively, for detecting whether said insertion and pusher means is operatively engaged to said flexible member as said probe carrier is driven through said tube.

* * * * *